United States Patent [19]
Karady et al.

[11] Patent Number: 6,072,094
[45] Date of Patent: Jun. 6, 2000

[54] EFFICIENT SYNTHESIS OF CYCLOPROPYLACETYLENE

[75] Inventors: Sandor Karady, Mountainside; Benjamin Marcune, Neshanic Station, both of N.J.

[73] Assignee: Merck & Co., Inc., Rahway, N.J.

[21] Appl. No.: 09/128,637

[22] Filed: Jul. 28, 1998

Related U.S. Application Data

[60] Provisional application No. 60/054,860, Aug. 6, 1997.

[51] Int. Cl.⁷ .............................. C07C 1/207; C07C 2/02; C07C 2/00
[52] U.S. Cl. ........................... 585/538; 585/359; 585/534
[58] Field of Search ............................. 585/20, 359, 534, 585/538

[56] References Cited

U.S. PATENT DOCUMENTS

| | | | |
|---|---|---|---|
| 5,519,021 | 5/1996 | Young et al. | 514/230.5 |
| 5,633,405 | 5/1997 | Thompson et al. | 564/321 |
| 5,663,169 | 9/1997 | Young et al. | 514/230.5 |
| 5,663,467 | 9/1997 | Thompson et al. | 585/359 |
| 5,665,720 | 9/1997 | Young et al. | 514/230.5 |
| 5,698,741 | 12/1997 | Thompson et al. | 564/389 |
| 5,811,423 | 9/1998 | Young et al. | 514/230.5 |

FOREIGN PATENT DOCUMENTS

| | | |
|---|---|---|
| WO 95/20389 | 8/1995 | WIPO . |
| WO 96/22955 | 8/1996 | WIPO . |
| WO 96/37457 | 11/1996 | WIPO . |

OTHER PUBLICATIONS

P. H. Mazzocchi et a., J. Org. Chem, 43(15), p 3080–3083 (1978).
D. J. Peterson, J. Org. Chem., 33(2), p 780–784 (1968).
F. A. Carey & A. S. Court, J. Org. Chem., 37(12), p 1926–19269(1972).
J. Salaun, J. Org. Chem., 41(7), p 1237–1240(1976).
H. C. Militzer et al., Synthesis, p 998–1012 (1993).
A. S. Thompson et al., Tetrahedron Letters, 36(49) p 8937–8940 (1995).
C.E. Hudson et al., J. Chem. Soc., 94(4), p 1158 (1972).
W. Schoberth et al., Synthesis p 703 (1972).

*Primary Examiner*—Walter D. Griffin
*Assistant Examiner*—Tam M. Nguyen
*Attorney, Agent, or Firm*—S. A. Ayler; K. R. Walton; M. Winokur

[57] ABSTRACT

An efficient and facile process for the preparation of cyclopropylacetylene from thioanisole and cyclopropyl substituted ketones or aldehydes is disclosed.

7 Claims, No Drawings

EFFICIENT SYNTHESIS OF CYCLOPROPYLACETYLENE

This application claims the benefit of U.S. Provisional Application No. 60/054,860, filed on Aug. 6, 1997.

BACKGROUND OF THE INVENTION

A key step in the synthesis of the reverse transcriptase inhibitor, (-)-6-chloro-4-cyclopropylenthynyl-4-triflouromethyl-1,4-dihydro-2H-3,1-benzoxazin-2-one, also known as DMP-266, is the chiral addition to the 2-flouromethylcarbonyl-4-choloroanaline using cyclopropyl acetylene as a nucleophile, a chiral additive, a non-chiral additive, and an organic.

The syntheses of DMP-266 and structurally similar reverse transcriptase inhibitors are disclosed in U.S. Pat. No. 5,519,021, and the corresponding PCT International Patent Application WO 95/20389, which published on Aug. 3, 1995. Additionally, the asymmetric synthesis of an enantiomeric benzoxazinone by a highly enantioselective acetylide addition and cyclization sequence has been described by Thompson, et al., Tetrahedron Letters 1995, 36, 8937–8940, as well as the PCT publication, WO 96/37457, which published on Nov. 28, 1996.

Additionally, several applications have been filed which disclose various aspects of the synthesis of (-)-6-chloro-4-cyclopropylethynyl-4-triflouromethyl-1,4-dihydro-2H-3,1-benzoxazin-2-one, including: 1) a process for the preparation of cyclopropylacetylene by cyclizing 5-halo-1-pentyne published on Aug. 1, 1996 in PCT Publication No. WO 96/22955; 2) a process for making the chiral alcohol, U.S. Ser. No. 60/035,462, filed Jan. 14, 1997; 3) the chiral additive, U.S. Ser. No. 60/034,926, filed Jan. 10, 1997; 4) the cyclization reaction, U.S. Ser. No. 60/037,059, filed Feb. 12, 1997; 5) the anti-solvent crystallization procedure, Case No. 19905PV2 (U.S. Serial No. unknown), filed May 23, 1997.

Several methods have been described in published literature for preparation of cyclopropylacetylene. C. E. Hudson and N. L. Bauld, J.A.C.S. 94:4, p.1158 (1972); J. Salaun, J.O.C. 41:7 p.1237 (1976); and W. Schoberth and M. Hanack, Synthesis (1972). p.703 disclose methods for the preparation of cyclopropylacetylene by dehydrohalogenating 1-cyclopropyl-1,1-dichloroethane. Miltzer, H. C. et al., Synthesis, 998 (1993) disclose a method for preparation of cyclopropylalkenes by halogenating an enolether, reacting the alkyl 1,2-dihaloether with propargyl magnesium bromide, and cyclizing to give a 2-alkoxy-1-ethynylcyclopropane. F. A. Carey and A. S. Court, J. Org. Chem., Vol. 37, No.12, (1972) p. 1926 disclose the use of a modified Wittig-Horner olefin synthesis for organcic transformations; D. J. Peterson, J. Org. Chem., Vol. 20C, No. 33, (1968) p. 780 describes the application of olfenation to make vinyl sulfides and H. Takeshita and T. Hatsui, J. Org. Chem., Vol. 43, No. 15, (1978) p. 3083 disclose the use of potassium 3-aminopropylamide in base-catalyzed prototropic reactions.

As illustrated by the Scheme below, Schoberth, et al., describes a method which resulted in about a 42% yield of the cyclopropylacetylene.

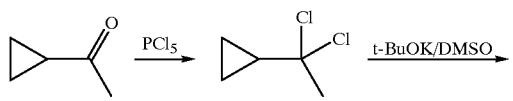

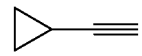

The instant invention discloses a more efficient process for the synthesis of this important substrate.

SUMMARY OF THE INVENTION

The present invention relates to a process for the preparation of cyclopropyl acetylene (CPA), represented by formula I:

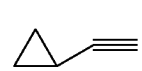

I which comprises reacting thioanisole represented by formula II:

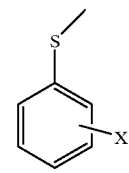

II wherein X is H, halo, $CF_3$, or $C_{1-6}$ alkyl;

in the presence of a base and a silylating agent, to a compound represented by formula III:

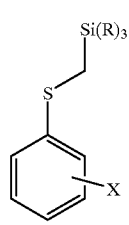

III wherein each R is independently a $C_{1-6}$ alkyl and X is described above;

reacting a compound of formula III with a compound of formula IV:

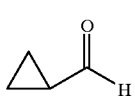

IV in the presence of a base to yield vinyl thioethers, represented by formula V and VI:

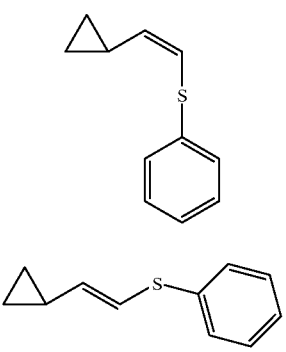

reacting a compound of formula V and VI in the presence of potassium diaminopropane (KAPA) to yield cyclopropyl acetylene.

This process is a more facile and efficient alternative to known synthetic pathways insofar as the entire scheme can be carried out in a single eaction vessel by sequential addition of the required reagents.

DETAILED DESCRIPTION OF THE INVENTION

The instant invention relates to a process for the preparation of cyclopropyl acetylene (CPA), represented by formula I:

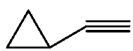

First, a solution of thioanisole, represented by formula II:

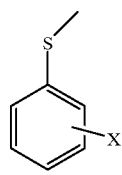

wherein X is H, halo, $CF_3$, or $C_{1-6}$ alkyl;
is reacted in the presence of a base and a silylating agent to yield a compound represented by formula III:

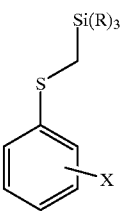

wherein X and R are described above,

For purposes of this invention, the base employed is an alkyl lithium such as phenyl lithium, Butyl lithium (BuLi) or a potassium alkyl such as potassium methyl and the like, preferably BuLi and the silylating agent employed is selected from the group consisting of trialkylsilylchlorides, triakylsilyliodides and triflates such as trimethylsilylchloride, triethylsilylchloride, t-butyldimethylsilyl chloride, t-butyldiphenylsilylchloride, trimethylsilyltriflate, t-butyldimethylsilyltriflate, triethylsilyltriflate, triethylsilyliodide and the like, preferably trimethylsilylchloride (TMSCl). The solution of thioanisole, consisting of thioanisole and a protic solvent such as tetrahydrofuran (THF), is cooled to a temperature of about −100° C. to about −60° C., preferably −95° C. to about −70° C. before contact with the strong base. Upon contact with the base the solution is warmed to a temperature of about −5° C. to about 5° C., preferably about −2° C. to about 1° C. for approximately 10 minutes to about one hour and then cooled to a temperature of about −100° C. to about −60° C. preferably −95° C. to about −70° C. before contact with the silylating agent. After addition of the silyating agent the mixture is warmed to a temperature of about −5° C. to about 5° C., preferably about −2° C. to about 1° C. for approximately 10 minutes to about one hour.

Next, Compound III is reacted with a compound of formula IV:

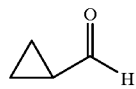

in the presence of a base to yield vinyl thioethers, represented by formula V and VI:

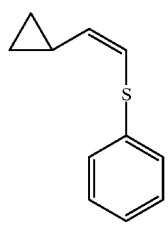

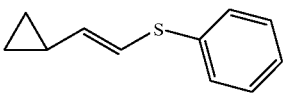

For purposes of this invention, the base employed is an alkyl lithium such as phenyl lithium, Butyl lithium (BuLi) or a potassium alkyl such potassium methyl and the like, preferably BuLi. The solution of Compound III is cooled to a temperature of about −100° C. to about −60° C., preferably −95° C. to about −70° C. before contact with compound IV.

Finally, Compound V and VI are then reacted in the presence of potassium diaminopropane (KAPA) to yield the desired product, cyclopropyl acetylene (CPA).

The term alkyl relates to lower alkyls such as methyl, ethyl, isopropyl, butyl, propyl and the like.

The term halo relates to fluoro, chloro, iodo and bromo.

CPA can be isolated, after aqueous quench of the reaction, by extraction into an organic solvent, such a s hexane or toluene. Alternatively, CPA can be isolated and purified by distillation.

The reagents used in this process are either commercially available or may be prepared by synthetic methods commonly known in the art. KAPA may be generated from KH and diamino propane by methods known in the art.

Some of the intermediate compounds synthesized in the present invention occur as geometric isomers. The processes of synthesizing all such isomers are included in the present invention.

In another preferred aspect of this invention, Compound IV is cyclopropyl carboxaldehyde.

The present invention is embodied by the following non-limiting example.

EXAMPLE

Reaction Scheme

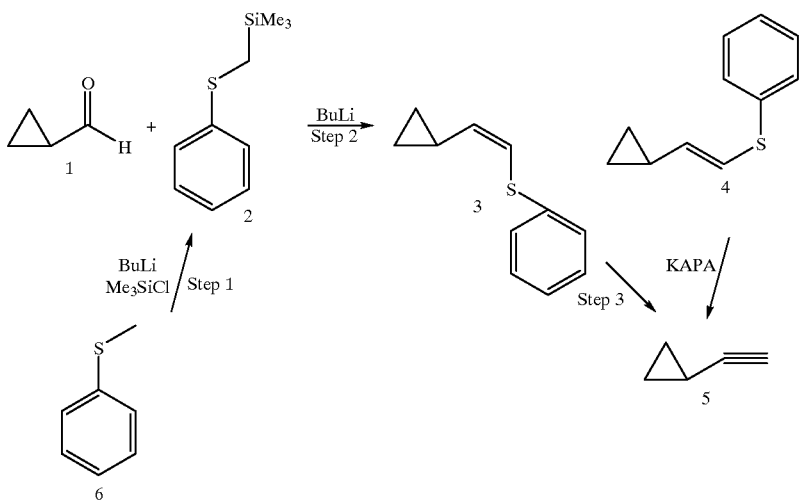

Procedure

Step 1

A solution of thioanisole (4.7 g, 1.05 mmoles) in 19 ml of THF was cooled to −78° C. and a hexane solution of butyl lithium (14.5 ml 2.05 mmoles) was added and the solution was warmed to 0° C. for 30 minutes to complete anion formation. After this the solution was cooled to −78° C. and trimethylsilyl chloride (4 g, 1.03 mmoles) was added, followed by warming to 0° C. for 30 minutes.

Step 2

The resulting mixture was cooled again to −78° C. before another portion of butyl lithium (14.4 ml, 2.05 mmole) was added. After warming and aging at 0° C. for 30 minutes, cyclopropyl carboxaldehyde(2.5 g, 1.0 mmole) was added at −78° C. The mixture was stirred overnight at room temperature and then quenched with 100 ml of water. The organic product was extracted with 40 ml of hexane followed by evaporation. The NMR spectrum indicated that a mixture of E and Z thiovinyl ethers 3 and 4 were produced.

Alternatively, commercially available TMS thioanisole may be employed and the reaction initiated at Step 2 according to the following procedure:

A solution of (phenylthiomethyl)trimethylsilane 2 ml (10 mmole) in THF(5 ml) was cooled to −78° C. and a hexane solution of butyllithium (4.5 ml ,2.25 mmoles) was added. The solution was allowed to warm to room temperature, then it was cooled again to −78° C. and cyclopropane carboxaldehyde (0.75 ml, 10 mmole) was added dropwise. The reaction mixture was kept at −78° C. for an additional two hours and then it was allowed to warm to room temperature. The mixture was extracted with water and the solvent was removed to give an oil. The NMR spectrum of this mixture was identical with that of the product obtained for synthesized TMS thioanisole, as described above. This mixture was used without purification for the next step.

Step 3

A solution of the mixture of the vinyl sulfides 3 and 4, from the previous reactions, (176 mg, 0.85 mm) in diaminopropane (1 ml) was cooled with ice and a solution of KAPA (potassium diaminopropane, 2 mmoles) in 2 ml of diaminopropane was added. After this the solution was allowed to stir at room temperature for 18 hr. A GC assay indicated that 41 mg cyclopropyl acetylene was produced in 62% yield.

What is claimed is:

1. A process for the preparation of cyclopropyl acetylene (CPA), represented by formula I:

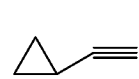
I which comprises reacting a compound represented by formula II:

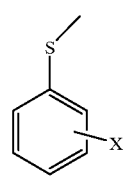
II wherein X is H, halo, $CF_3$, or $C_{1-6}$ alkyl;

in the presence of a base and a silylating agent, to a compound represented by formula III:

which comprises reacting a compound of formula II:

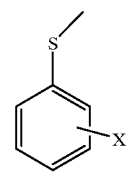

wherein X is H, halo, $CF_3$, or $C_{1-6}$ alkyl;
in the presence of BuLi and TMSCl, to a compound represented by formula III:

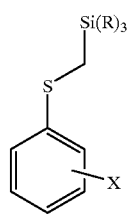

wherein each R is independently a $C_{1-6}$ alkyl and X is described above;

reacting a compound of formula III with a compound of formula IV:

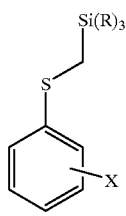

wherein each R is independently a $C_1$ alkyl and X is described above;

reacting a compound of formula III with a cyclopropyl carboxaldehyde, represented by formula IV:

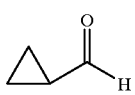

in the presence of a base to yield a vinyl thioether, represented by formula V and VI:

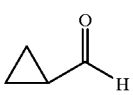

in the presence of BuLi to yield vinyl thioethers, represented by formula V and VI:

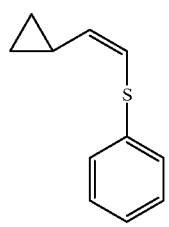

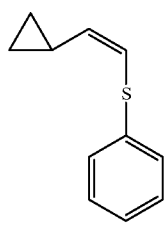

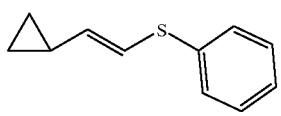

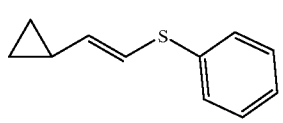

reacting a compound of formula V and VI in the presence of potassium diaminopropane (KAPA) to yield cyclopropyl acetylene.

2. The process of claim 1 wherein the base employed is phenyl lithium, Butyl lithium (BuLi) or potassium methyl and the compound of formula II is reacted with the base at a temperature of about −100° C. to about −60° C.

3. The process according to claim 2 wherein the temperature is about −95° C. to about −70° C. and the base is BuLi.

4. The process of claim 1 wherein the silylating agent employed are trialkylsilylchlorides, triakylsilyliodides and triflates.

5. The process of claim 4 wherein the silylating agents are trimethylsilylchloride, triethylsilylchloride, t-butyldimethylsilyl chloride, t-butyldiphenylsilylchloride, trimethylsilyltriflate, t-butyldimethylsilyltriflate, triethylsilyltriflate, and triethylsilyliodide.

6. The process of claim 5 wherein the silylating agent is trimethylsilylchloride.

7. A process for the preparation of cyclopropyl acetylene (CPA), represented by formula I:

reacting a compound of formula V and VI in the presence of potassium diaminopropane (KAPA) to yield cyclopropyl acetylene.

* * * * *